US012758115B2

(12) United States Patent
Faust et al.

(10) Patent No.: US 12,758,115 B2
(45) Date of Patent: Oct. 13, 2026

(54) MAGNETIC RESONANCE TOMOGRAPHY UNIT FOR LOCALIZING METALLIC OBJECTS AND OPERATING METHOD

(71) Applicant: Siemens Healthineers AG, Forchheim (DE)

(72) Inventors: Jonas Faust, Leonberg (DE); Peter Speier, Erlangen (DE); Florian Maier, Buckenhof (DE)

(73) Assignee: Siemens Healthineers AG, Forchheim (DE)

( * ) Notice: Subject to any disclaimer, the term of this patent is extended or adjusted under 35 U.S.C. 154(b) by 156 days.

(21) Appl. No.: 18/666,027

(22) Filed: May 16, 2024

(65) Prior Publication Data

US 2024/0382103 A1 Nov. 21, 2024

(30) Foreign Application Priority Data

May 16, 2023 (EP) .................................... 23173593

(51) Int. Cl.
*A61B 5/055* (2006.01)
*G01R 33/48* (2006.01)
*G01R 33/565* (2006.01)

(52) U.S. Cl.
CPC .......... *A61B 5/055* (2013.01); *G01R 33/4818* (2013.01); *G01R 33/56545* (2013.01)

(58) Field of Classification Search
CPC .......... G01R 33/4818; G01R 33/56545; A61B 5/055
See application file for complete search history.

(56) References Cited

U.S. PATENT DOCUMENTS

| | | | | |
|---|---|---|---|---|
| 11,204,399 B2 * | 12/2021 | Cunningham | ..... | G01R 33/5608 |
| 11,762,047 B2 * | 9/2023 | Schneider | .............. | G01R 33/48 324/309 |
| 11,940,516 B2 * | 3/2024 | Liu | .................... | G01R 33/4824 |
| 2016/0349335 A1 | 12/2016 | Olsen | | |

(Continued)

FOREIGN PATENT DOCUMENTS

| | | | | |
|---|---|---|---|---|
| DE | 102018215618 B3 | 12/2019 | | |
| EP | 3799063 A1 * | 3/2021 | ............. | G16H 30/40 |

(Continued)

OTHER PUBLICATIONS

Bakker, Chris JG, Jan-Henry Seppenwoolde, and Koen L. Vincken. "Dephased MRI." Magnetic Resonance in Medicine: An Official Journal of the International Society for Magnetic Resonance in Medicine 55.1 (2006): 92-97.

(Continued)

*Primary Examiner* — Gregory H Curran
(74) *Attorney, Agent, or Firm* — Lempia Summerfield Katz LLC

(57) ABSTRACT

A magnetic resonance tomography unit for localizing metallic objects and an operating method are provided. In one act of the method, an excitation pulse is used to excite nuclear spins in a region surrounding a compact metallic object. Magnetic resonance data is acquired with samplings along a plurality of trajectories, where the samplings take place using a bSSFP sequence, and the nuclear spins are dephased by a gradient. A position of a geometric focal point of the compact metallic object is ascertained based on a position of a visual focal point of acquired artifacts.

15 Claims, 4 Drawing Sheets

(56) References Cited

U.S. PATENT DOCUMENTS

2020/0085381 A1 3/2020 Weine
2024/0069137 A1 2/2024 Faust

FOREIGN PATENT DOCUMENTS

EP 4253977 A1 10/2023
EP 4332602 A1 3/2024

OTHER PUBLICATIONS

Bartels, Lambertus W., et al. "MR imaging of vascular stents: effects of susceptibility, flow, and radiofrequency eddy currents." Journal of Vascular and Interventional Radiology 12.3 (2001): 365-371.
Bieri, Oliver, and Klaus Scheffler. "Fundamentals of balanced steady state free precession MRI." Journal of Magnetic Resonance Imaging 38.1 (2013): 2-11.
Butts, Kim, et al. "Management of Biopsy Needle Artifacts: Techniques for RF-Refocused MRI." Journal of Magnetic Resonance Imaging: An Official Journal of the International Society for Magnetic Resonance in Medicine 9.4 (1999): 586-595.
Chan, Rachel W., et al. "Temporal stability of adaptive 3D radial MRI using multidimensional golden means." Magnetic Resonance in Medicine: An Official Journal of the International Society for Magnetic Resonance in Medicine 61.2 (2009): 354-363.
Cunningham, Charles H., et al. "Positive contrast magnetic resonance imaging of cells labeled with magnetic nanoparticles." Magnetic Resonance in Medicine: An Official Journal of the International Society for Magnetic Resonance in Medicine 53.5 (2005): 999-1005.
Dahnke, Hannes, et al. "Susceptibility gradient mapping (SGM): a new postprocessing method for positive contrast generation applied to superparamagnetic iron oxide particle (SPIO)-labeled cells." Magnetic resonance in medicine 60.3 (2008): 595-603.
De Leeuw, H., P. R. Seevinck, and C. J. G. Bakker. "Center-Out Radial Sampling with Off-resonant Reconstruction for Efficient and Accurate Localization of Punctate and Elongated Paramagnetic Structures." Magnetic resonance in medicine 69.6 (2013): 1611-1622.
Diwoky, Clemens, et al. "Positive contrast of SPIO-labeled cells by off-resonant reconstruction of 3D radial half-echo bSSFP." NMR in Biomedicine 28.1 (2015): 79-88.
Faust, Jonas F., et al. "Fast 3D Passive Needle Localization for MR-Guided Interventions using Radial White Marker Acquisitions and CNN Postprocessing." Proc. Intl. Soc. Mag. Reson. Med. 30 (2022).
Glowinski, Arndt, et al. "A perspective on needle artifacts in MRI: an electromagnetic model for experimentally separating susceptibility effects." IEEE transactions on medical imaging 19.12 (2000): 1248-1252.
Huisman, Henkjan J., et al. "Prostate cancer: precision of integrating functional MR imaging with radiation therapy treatment by using fiducial gold markers." Radiology 236.1 (2005): 311-317.
Ladd, Mark E., et al. "Biopsy needle susceptibility artifacts." Magnetic resonance in medicine 36.4 (1996): 646-651.
Lagerburg, V., et al. "Simulation of the artefact of an iodine seed placed at the needle tip in MRI-guided prostate brachytherapy." Physics in Medicine & Biology 53.5 (2008): N59.
Lauer, Ulrike A., et al. "Radio frequency versus susceptibility effects of small conductive implants—a systematic MRI study on aneurysm clips at 1.5 and 3 T." Magnetic resonance imaging 23.4 (2005): 563-569.
Miquel, M. E., et al. "Using combined x-ray and MR imaging for prostate I-125 post-implant dosimetry: phantom validation and preliminary patient work." Physics in Medicine & Biology 51.5 (2006): 1129.
Moerland, Marinus A., et al. "Evaluation of permanent I-125 prostate implants using radiography and magnetic resonance imaging." International journal of radiation oncology, biology, physics 37.4 (1997): 927-933.
Müller-Bierl, Bernd, et al. "Numerical modeling of needle tip artifacts in MR gradient echo imaging." Medical physics 31.3 (2004): 579-587.
Patil, Sunil, Oliver Bieri, and Klaus Scheffler. "Echo-dephased steady state free precession." Magnetic Resonance Materials in Physics, Biology and Medicine 22 (2009): 277-285.
Petersen, Erika A., et al. "Minimizing brain shift in stereotactic functional neurosurgery." Operative Neurosurgery 67.3 (2010): ons213-ons221.
Ronneberger, Olaf, Philipp Fischer, and Thomas Brox. "U-net: Convolutional networks for biomedical image segmentation." Medical image computing and computer-assisted intervention-MICCAI 2015: 18th international conference, Munich, Germany, Oct. 5-9, 2015, proceedings, part III 18. Springer International Publishing, 2015.
Scheffler, Klaus, and Jürgen Hennig. "Is TrueFISP a gradient-echo or a spin-echo sequence?. " Magnetic Resonance in Medicine: An Official Journal of the International Society for Magnetic Resonance in Medicine 49.2 (2003): 395-397.
Seevinck, Peter R., et al. "Highly localized positive contrast of small paramagnetic objects using 3D center-out radial sampling with off-resonance reception." Magnetic resonance in medicine 65.1 (2011): 146-156.
Seppenwoolde, Jan-Henry, Max A. Viergever, and Chris JG Bakker. "Passive tracking exploiting local signal conservation: the white marker phenomenon." Magnetic Resonance in Medicine: An Official Journal of the International Society for Magnetic Resonance in Medicine 50.4 (2003): 784-790.
Shellock, Frank G., Matthew Gounis, and Ajay Wakhloo. "Detachable coil for cerebral aneurysms: in vitro evaluation of magnetic field interactions, heating, and artifacts at 3T." American Journal of Neuroradiology 26.2 (2005): 363-366.
Sinha, S., et al. "Pulse sequence optimization for use with a biopsy needle in MRI." Magnetic resonance imaging 7.5 (1989): 575-579.
Stuber, Matthias, et al. "Positive contrast visualization of iron oxide-labeled stem cells using inversion-recovery with ON-resonant water suppression (IRON)." Magnetic Resonance in Medicine: An Official Journal of the International Society for Magnetic Resonance in Medicine 58.5 (2007): 1072-1077.
Teitelbaum, G. P., W. G. Bradley Jr, and B. D. Klein. "MR imaging artifacts, ferromagnetism, and magnetic torque of intravascular filters, stents, and coils." Radiology 166.3 (1988): 657-664.
Van der Weide, Remko, Chris JG Bakker, and Max A. Viergever. "Localization of intravascular devices with paramagnetic markers in MR images." IEEE Transactions on medical imaging 20.10 (2001): 1061-1071.
Vonken, Evert-jan PA, Michael Schär, and Matthias Stuber. "Positive contrast visualization of nitinol devices using susceptibility gradient mapping." Magnetic resonance in medicine 60.3 (2008): 588-594.
Weine, Jonathan, et al. "Interleaved White Marker Contrast with bSSFP Real-Time Imaging for Deep Learning based Needle Localization in MR-Guided Percutaneous Interventions." Proceedings of the 27th Annual Meeting of ISMRM, Montreal. 2019.
Weine, Jonathan, et al. "Passive Needle Tracking with Deep Convolutional Neural Nets for MR-Guided Percutaneous Interventions." Proceedings of 12th Interventional MRI Symposium Oct. vol. 12. 2018.
Wikipedia "Steady-state free precession imaging." Wikipedia, The Free Encyclopedia. Wikipedia, The Free Encyclopedia, Nov. 21, 2022. Web. May 3, 2024.
Weine, Jonathan "Deep Learning based Passive Needle Tracking for MR-Guided Percutaneous Interventions" Dec. 2018. pp. 1-85.

* cited by examiner

MAGNETIC RESONANCE TOMOGRAPHY UNIT FOR LOCALIZING METALLIC OBJECTS AND OPERATING METHOD

This application claims the benefit of European Patent Application No. EP 23173593.7, filed on May 16, 2023, which is hereby incorporated by reference in its entirety.

BACKGROUND

Independent of the grammatical term usage, individuals with male, female, or other gender identities are included within the term.

Magnetic resonance tomography units are imaging apparatuses that, for mapping an examination object, align nuclear spins of the examination object with a strong external magnetic field and, via an alternating magnetic field, excite the nuclear spins to precession about this alignment. The precession or the return of the spins from this excited state into a state with lower energy thus generates an alternating magnetic field as the response, which is received via antennae.

With the aid of magnetic gradient fields, a position encoding is impressed upon the signals, which subsequently enables an allocation of the received signal to a volume element. The received signal is then analyzed, and a three-dimensional imaging representation of the examination object is provided. For receiving the signal, local receiving antennae (e.g., local coils) that, in order to achieve a better signal-to-noise ratio, are arranged directly on the examination object may be used.

A magnetic resonance tomography unit enables the inside of the body to be visualized over an extended time without exposing the patient or operator to an increased dose of ionizing radiation. The use of the magnetic resonance tomography unit for real-time monitoring is rendered difficult by the complex image acquisition and the slow image sequence associated therewith. Further, it is necessary to represent instruments that themselves not only generate no magnetic resonance signal but rather, on account of their metallic properties, hinder acquisition in the region surrounding the instrument in real time.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a magnetic resonance tomography unit and a method for operating the magnetic resonance tomography unit that enable a fast tracking of an instrument are provided.

The purpose of the method according to the present embodiments is to localize a compact metallic object using a magnetic resonance tomography unit.

In the present embodiments, an object is deemed to be compact in three dimensions if its dimensions in all spatial directions differ only insignificantly (e.g., by less than 50%, 20%, or 10%). A compact object of this kind may be a rotationally symmetrical sphere, as specified below. However, ellipsoids, polyhedrons, or, for example, also irregular bodies that fulfill this condition may also be provided.

In the context of the present embodiments, objects are deemed to be linear metallic objects that are compact in two dimensions if the objects extend essentially in a linear manner along an axis and their dimensions in a plane perpendicular to the axis in all spatial directions differ in this plane only insignificantly (e.g., by less than 50%, 20%, or 10%). An object of this kind may be a cylinder or hollow cylinder that is rotationally symmetrical to the axis. However, regular or irregular prisms, for example, may also be provided.

Objects of this kind are frequently used during interventions or the treatment of a patient. For example, a biopsy needle is typically circular-cylindrical in shape with an axis of symmetry for a rotation about this axis, where the axis of symmetry extends centrally along the biopsy needle. In addition, seeds are used for marking or radiotherapy. In the case of radiotherapy, the seeds are filled with a radioactive isotope. These seeds may be spherical or cylindrical in shape.

In one act of the method according to the present embodiments, the magnetic resonance tomography unit uses a radiofrequency pulse to excite nuclear spins in a region surrounding the compact metallic object to precession about a vector of a magnetic field in the region surrounding the metallic object. The magnetic field may be determined by the static magnetic field of a field magnet, onto which a gradient field may be superimposed for slice selection. The frequency of the radiofrequency pulse results from the magnetic moment of the nuclear spins and the strength of the magnetic field, and is referred to as the Larmor frequency. The field strength and duration of the excitation pulse are determined by the degree of excitation to be achieved or the flip angle of the spins.

To suppress the background (e.g., the surrounding tissue), in one act, the magnetic resonance tomography unit uses a magnetic field gradient to dephase nuclear spins that are not located in the region immediately surrounding the metallic object and therefore are not influenced by a susceptibility change brought about by the compact metallic object. A gradient of this kind is also referred to as a white marker gradient, as the gradient leads to the effect that only the immediate surrounding region is not dephased by the white marker gradient on account of the Larmor frequency changed by the susceptibility fluctuation, or, more precisely, the external white marker gradient counteracts the local, susceptibility-induced gradient and reverses the dephasing. A magnetic resonance signal in the region immediately surrounding the metallic object thus supplies a signal with high contrast in comparison with the dephased background.

In a further act, the magnetic resonance tomography unit acquires magnetic resonance data along a plurality of trajectories. A trajectory refers to a curve or also, for example, a straight line in the k-space, along which magnetic resonance data is acquired or sampled. The sampling may take place at regularly spaced points along the curve. Within the scope of the present embodiments, the term trajectory is not the sum of all motion curves required for the mapping but, instead, individual contiguous sections that are also referred to as "readouts." For the radial sampling discussed, for example, the individual spokes are referred to as trajectories.

The sampling along the trajectories takes place within the framework of a balanced steady-state free precession (SSFP) sequence, as is known, for example, from https://en.wikipedia.org/wiki/Steady-state_free_precession_imaging.

The signals of the plurality of samplings are used to map an artifact produced by the compact metallic object in the position space. Using a reconstruction method, the magnetic resonance tomography unit or a separate reconstruction computer may generate a mapping of the artifacts generated by the compact metallic object in the position space from the measured values in the k-space.

On account of the dephasing with the white marker pulse, only the artifacts caused by the metallic object are represented in the mapping.

In one act, the magnetic resonance tomography unit or the controller thereof ascertains a position of the compact metallic object by determining the visual focal point of the image points of the artifact in the mapping. During visual focusing, the individual image points or voxels may be multiplied by a weighting function that may, for example, be given by the brightness value of the individual image point or is formed as a function thereof. A threshold value function that assumes the value zero when the brightness of an image point lies below a predetermined threshold value and the value 1 when the brightness lies above the threshold value may be provided, for example. The visual focal point therefore differs from a mass focal point and a geometric focal point. To ascertain a mass focal point, the position vector is weighted with a mass element during averaging. The geometric focal point is determined by an outer contour or a contour of an enclosure, and not by an internal mass distribution. For the compact metallic objects such as sphere, hollow sphere, needle, and hollow needle, however, the geometric focal point and the mass focal point are the same.

For the reasons explained below with reference to the advantages, the ascertained position of the visual focal point of the metallic object corresponds to the position of the geometric focal point of the object.

In one embodiment, the dephasing with the white marker gradient eliminates the background through the surrounding tissue, which would corrupt the ascertainment of the instrument position using the visual focal point of the signal. The artifact generated by the metallic object is thus separated from effects caused by the surrounding region in the acquired mapping, and the effects therefore do not need to be considered in subsequent acts.

Without this background, the artifact is displaced during a sampling by a bSSFP sequence along the same trajectory in opposite directions or over the trajectories that are distributed evenly over the spatial angle in each case symmetrically or by the same distance relative to the true position, so that the true position results from the averaging or visual focusing in the mapping.

It has been found that the bSSFP sequence may generate a symmetrical white marker artifact independently of a polarity of the white marker gradient. With the use of FLASH contrast, the artifact may be dependent on the polarity of the white marker gradient, and a twofold sampling with opposite polarity may be necessary in order to produce the same symmetry as with bSSFP.

Only through this background suppression may the real position of the metallic object be determined precisely by simple focal point ascertainment without detailed knowledge of the dislocation resulting from the susceptibility difference on the metallic object.

In this way, the method may make it possible to determine the real position of the mapped object without precise knowledge of the dislocation resulting from the susceptibility difference.

The apparatus according to the present embodiments shares the advantages of the method according to the present embodiments.

In one embodiment of the method, the compact metallic object is spherically symmetrical, and the sampling is a 3D sampling of a volume with the object. In other words, the trajectories of the sampling span a three-dimensional space. For example, a sampling along three trajectories may be provided. The three trajectories are perpendicular to each other and specify a Cartesian coordinate system.

For a spherically symmetrical or at least almost spherically symmetrical compact metallic object with essentially same dimensions in all spatial directions, it is possible to determine the position with a single 3D sampling. An object may be considered spherically symmetrical, for example, if the object fulfills the conditions specified above for a metallic object that is compact in three dimensions; this applies, for example, to spheres in the geometric sense. This is fulfilled, for example, for seeds.

In one possible embodiment of the method, the compact metallic object is a linear metallic object that is compact in two dimensions in accordance with the definition previously given. The compact metallic object accordingly has an axis along which the object extends. The object may have the greatest dimension along this axis. Two planes are arranged spaced apart from one another along this axis. The planes may be parallel to one another, but it is also possible that the planes enclose an angle greater than zero degrees with one another and intersect one another. A line of intersection of the planes may then have a distance from the axis that is greater than the longitudinal extension of the object or the distance between the planes along the axis (e.g., greater than a multiple of the longitudinal extension). The controller or the magnetic resonance tomography unit may receive these planes in a predetermined manner (e.g., in the form of a user input) or may also define the planes via an image acquisition, possibly with the error-prone position determination of the object. The only requirement is that the planes intersect the object.

For each of the planes, the magnetic resonance tomography unit or the controller thereof carries out a 2D sampling with the bSSFP sequence already described, and determines a focal point of the mapped artifact for each plane. The magnetic resonance tomography unit thereby receives two geometric points through which the linear compact metallic object extends. As already described, these are real geometric positions in which a position displacement by the susceptibility difference is already compensated. From these two points, the magnetic resonance tomography unit ascertains the axis or a straight line through the points on which the linear compact metallic object lies or along which the object extends.

In one embodiment, an alignment of the object in the space may be determined precisely by the two two-dimensional image acquisitions with the method.

In one embodiment of the method, the magnetic resonance data is acquired for a plurality of samplings along radial trajectories. The trajectories are evenly distributed in the angle over a full circle in a plane through the center of the k-space or over a sphere about the center of the k-space. A trajectory is referred to as a radial trajectory if its sampling points are arranged along a straight line through the center or the zero point of the k-space. Trajectories are referred to as evenly distributed if the trajectories have an equal angular spacing from one another. For example, in two dimensions (2D) in the case of a full circle, trajectories or straight lines are evenly distributed if the trajectories or straight lines have an angular spacing of 360 degrees divided by a natural number n where $n>2$. The number may, for example, also be uneven. In the three-dimensional space, for example, straight lines are evenly distributed if the straight lines extend through the center and a corner point of a uniform polyhedron about the center of the polyhedron and the k-space. A spiral arrangement of the readout direction over a hemisphere and then reversal of every second readout direction may also be provided, for example.

In one embodiment, the artifacts of an object in a mapping reconstructed from magnetic resonance data acquired along the evenly distributed trajectories are also distorted or displaced symmetrically to the object, so that these distortions are canceled out during focusing. The different orientation of the trajectories may result in an improved resolution in comparison with the embodiment described below.

In one possible embodiment of the method, the magnetic resonance data is sampled along the trajectories in both directions.

In one embodiment, as a result of the sampling in both directions, symmetrical distortions and displacements of the artifacts may, in each case, once again be generated and canceled out during focusing. However, no additional information resulting in a higher resolution is acquired in the case of sampling in two directions. For a comparable resolution in comparison with the embodiment described above with an even distribution, a greater number of samplings is therefore required. Trajectories that do not extend through the center (e.g., also, a sampling in a grid along Cartesian coordinates) may, however, also be provided.

The above-described characteristics, features, and advantages of this invention, as well as the manner in which these are achieved, will become clearer and more readily understandable in conjunction with the following description of the example embodiments, which are explained in more detail in conjunction with the drawings.

DETAILED DESCRIPTION

Figure 1:
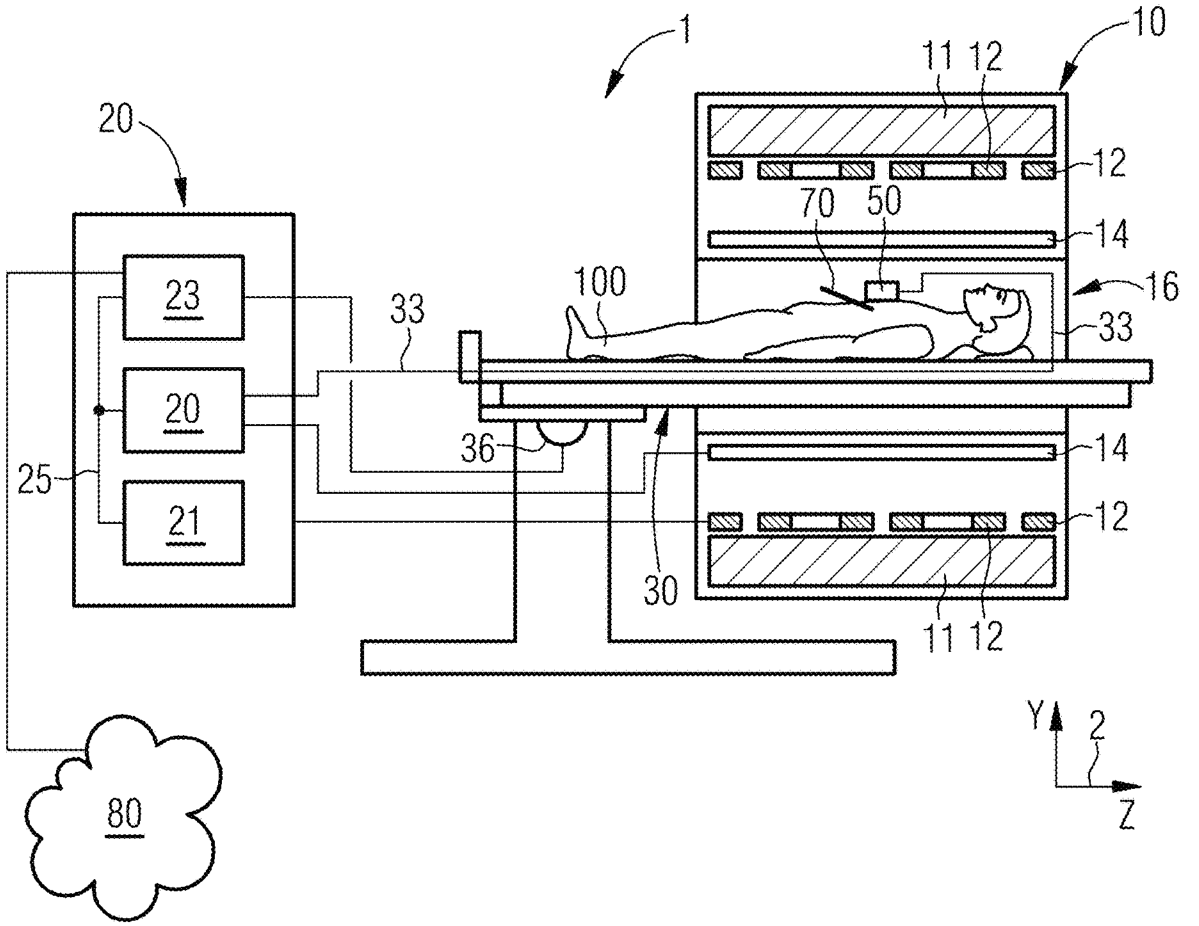
FIG. 1 shows a schematic representation of an embodiment of a magnetic resonance tomography unit for carrying out a method.

FIG. 1 shows a schematic representation of an embodiment of a magnetic resonance tomography unit 1 for carrying out a method according to the present embodiments.

A magnet unit 10 has a field magnet 11 that produces a static magnetic field B0 for aligning nuclear spins of samples or of a patient 100 in an acquisition region. The acquisition region is characterized by an extremely homogeneous static magnetic field B0. The homogeneity relates, for example, to the magnetic field strength or magnitude. The acquisition region is approximately spherical and located in a patient tunnel 16 that extends through the magnet unit 10 in a longitudinal direction 2.

A patient couch 30 may be moved inside the patient tunnel 16 by the travel unit 36.

Typically, the field magnet 11 is a superconducting magnet that may provide magnetic fields having a magnetic flux density of up to 3 T or even more in more recent devices. For lower field strengths, it is, however, possible to also use permanent magnets or electromagnets having normally conductive coils.

The magnet unit 10 also has gradient coils 12 that are configured to superimpose variable magnetic fields in three spatial directions on the magnetic field B0 for the purpose of spatial discrimination of the acquired mapping regions in the examination volume. The gradient coils 12 may be coils made of normally conductive wires that may generate mutually orthogonal fields in the examination volume.

The magnet unit 10 also has a body coil 14 that is configured to radiate a radiofrequency signal supplied via a signal line into the examination volume, to receive resonance signals emitted by the patient 100, and to output the resonance signals via a signal line. The term transmit antenna denotes below an antenna via which the radiofrequency signal is emitted for exciting the nuclear spins. This may be the body coil 14, but may also be a local coil 50 having a transmit function.

A control unit 20 supplies the magnet unit 10 with the various signals for the gradient coils 12 and the body coil 14, and analyzes the received signals.

Thus, the control unit 20 has a gradient controller 21 that is configured to supply the gradient coils 12 via supply lines with variable currents that provide, coordinated in time, the desired gradient fields in the examination volume.

In addition, the control unit 20 has a radiofrequency unit 22 that is configured to produce a radiofrequency pulse having a predefined variation over time, amplitude, and spectral power distribution for the purpose of exciting magnetic resonance of the nuclear spins in the patient 100. Pulse powers in the kilowatt range may be achieved in this case. The excitation signals may be radiated via the body coil 14 or via a local transmit antenna into the patient 100.

A controller 23 communicates via a signal bus 25 with the gradient controller 21 and the radiofrequency unit 22.

A local coil 50 is arranged on the patient 100 and is connected to the radiofrequency unit 22 and its receiver via a connecting lead 33. In one embodiment, however, the body coil 14 may be a receiving antenna.

A compact metallic object 70 (e.g., a biopsy needle) may be inserted into the patient 100. There may, however, also be objects 70 in the body of the patient 100 that are already present there and the location of which is to be acquired. One example of such objects are seeds (e.g., capsules that contain a radiation source and are used for radiotherapy). Seeds may be reference markers for an X-ray examination or an irradiation controlled by X-ray acquisition. The precise geometric location relative to a tumor may be decisive. The object 70 is metallic and generates artifacts during magnetic resonance imaging, as alternating electromagnetic fields are attenuated. The metal also causes a change in the static or semistatic magnetic fields (e.g., the magnetic field B0 and the gradient fields) on account of its different susceptibility in comparison with the surrounding region. As a result, same magnetic field magnitudes occur at a number of (e.g., several) different geometric positions in the region surrounding the object and are mapped onto a common point via position encoding. In conventional image acquisition, the region surrounding the object is distorted by the variation in the magnetic field and transposed to a changed location relative to the surrounding organs.

The magnetic resonance tomography unit 1 may also be integrated via a signal connection to an external signal processing resource such as a cloud 80 as part of the system in which parts of the method according to the present embodiments are carried out.

Figure 2:
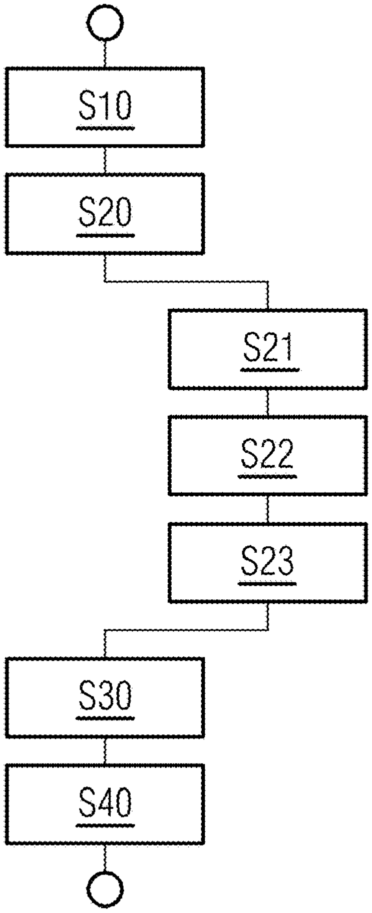
FIG. 2 shows a schematic flow diagram of an embodiment of a method.

FIG. 2 shows a schematic flow diagram of an embodiment of the method.

In act S10, the magnetic resonance tomography unit uses an excitation pulse to excite nuclear spins at least in a region surrounding the compact metallic object. The excitation takes place according to the present embodiments in accordance with the bSSFP sequence used.

The bSSFP sequence is characterized in that the zeroth gradient moment on all axes is reversed again (e.g., by all gradients that are played out after the excitation pulse being played out with opposite polarity before the next excitation).

In a further act S20, the magnetic resonance tomography unit 1 acquires magnetic resonance data by sampling along a radial trajectory 90.

The nuclear spins are dephased in act S21 by a gradient in order to hide the background of the body. Only the region immediately surrounding the object is not affected by the magnetic field changes produced by the susceptibility difference, as the duration and/or strength of the gradient is selected precisely so that the duration and/or strength of the gradient dephase the magnetic resonance signals in the unaffected, more remote tissue.

In act S22, the magnetic resonance tomography unit acquires MR signals with a sampling scheme along a radial trajectory 90 in the k-space.

Further, in act S23, the magnetic resonance tomography unit 1 acquires MR signals with a sampling scheme along the radial trajectory 90 in the opposite direction in the k-space.

Figure 3:
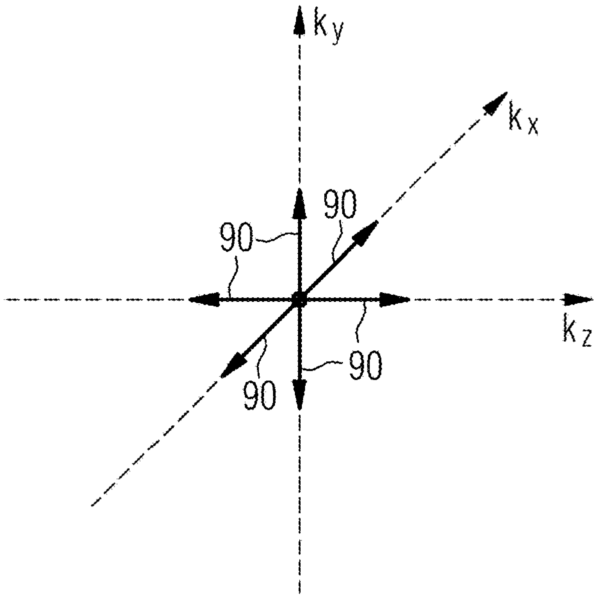
FIG. 3 shows a schematic example of a three-dimensional (3D) sampling scheme according to an embodiment in the k-space.

FIG. 3 schematically shows radial trajectories 90 in the k-space. The trajectories 90 extend through the center or the coordinate point of origin of the k-space. FIG. 3 also shows a three-dimensional (3D) sampling. A sampling takes place in all three spatial coordinates of the k-space and not just in one plane. Trajectories 90 along the coordinate axes are specified here by way of example. The sampling may, however, take place with any radial trajectories 90 that span a three-dimensional space for the 3D sampling or a two-dimensional (2D) space for the 2D sampling in the k-space. The number of the trajectories 90 may be greater (e.g., three times, ten times, or more), and the trajectories are distributed equally over all spatial directions or directions in the plane.

In one embodiment, as already described, radial trajectories 90 that are distributed evenly over a circle or a full sphere result in symmetrical delocalized artifacts in an image reconstructed therefrom, which cancel each other out in the image during focusing. This effect may, however, also be achieved for non-radial (e.g., Cartesian) trajectories if these are sampled in both directions in each case along the trajectory 90 during acquisition of the magnetic resonance signals.

An even distribution of the directions of the trajectory over a circle or a sphere enables a time saving with higher spatial resolution compared to sampling in opposite directions through acquisition of a number of (e.g., several) different k-space rows.

The acts S22 and S23 are repeated for each trajectory 90.

Then, in act S30, image reconstruction takes place with the acquired MR signals in the magnetic resonance tomography unit 1 or on an external device in the cloud 80. The generated images show the metallic object essentially without background through the surrounding tissue on account of the white marker gradient or the dephasing of the object 70, albeit with the already mentioned artifacts such as distortion and dislocation.

Finally, in act S40, a focal point of the mapping of the object 70 is determined. A weighting factor may be applied to the position vectors, corresponding, for example, to a brightness value of the corresponding pixel or voxel. A threshold value function that considers only image points with an amplitude greater than a predetermined threshold value may also be provided.

Radial trajectories 90 that are distributed evenly over a circle or sphere in the k-space also result in a distortion or dislocation in the image space that is distributed evenly over the directions, so that during the subsequent averaging, when the focal point is determined, these cancel each other out and are eliminated without quantitative knowledge of the distortion and dislocation when the focal point is determined.

A comparable effect may also be achieved through sampling of the trajectory 90 in both directions. In the bSSFP sequence used, this may result in a symmetrically mirrored distortion or dislocation in the image space, so that during the subsequent averaging, when the focal point is determined, these cancel each other out and are eliminated without quantitative knowledge of the distortion and dislocation when the focal point is determined.

The object 70 may then be output to a user by the magnetic resonance tomography unit with the actual position ascertained (e.g., in a mapping), or also as a navigation aid in optical, acoustic, or tactile form.

The sequence shown in FIG. 2 corresponds essentially to the method according to the present embodiments for a compact object 70 having essentially the same dimensions and, for example, also symmetries in all spatial directions (e.g., a sphere, a polyhedron, or also irregularly shaped compact bodies).

Figure 4:
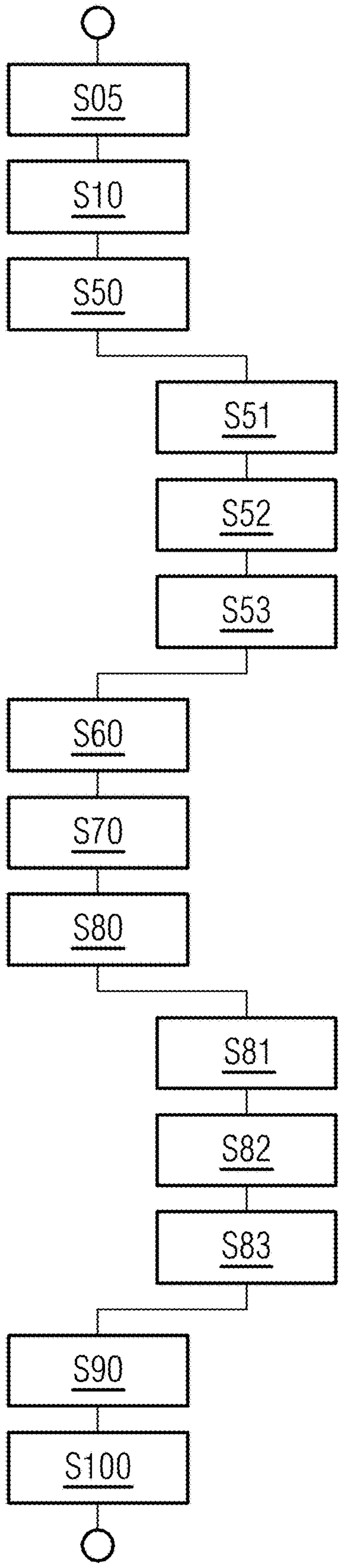
FIG. 4 shows a schematic flow diagram of an embodiment of the method.
Figure 5:
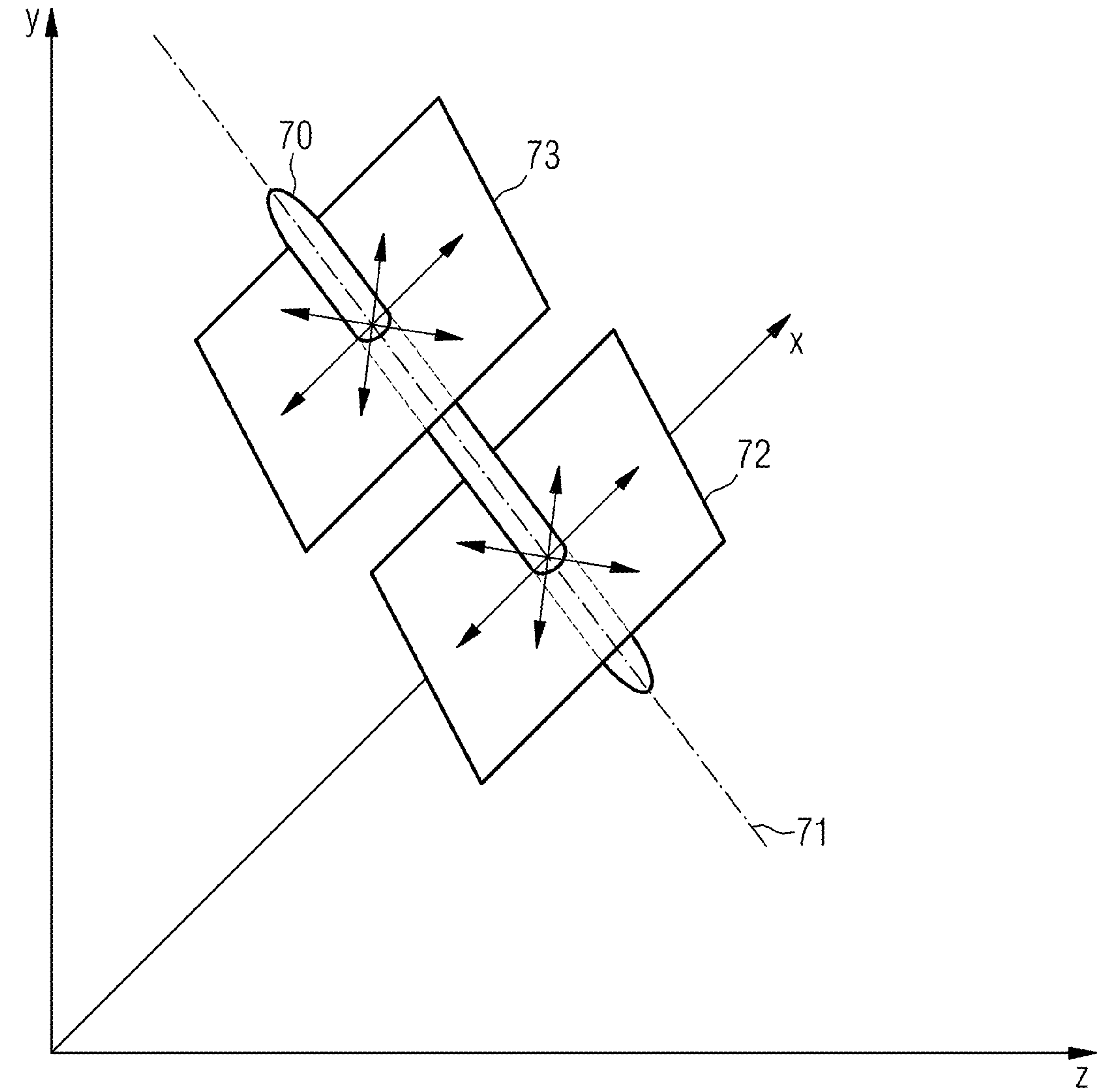
FIG. 5 shows a schematic example of a two-dimensional (2D) sampling scheme.

FIG. 4 shows a flow diagram of an embodiment of the method for a metallic object 70, as shown in FIG. 5. The object 70 in FIG. 5 extends along an axis 71. The extension along the axis is significantly greater than the dimensions of the object 70 at right angles to the axis 71. In the context of the present embodiments, an object 70 of this kind is referred to as linear and compact in two dimensions. This is apparent, for example, from the method sequence in FIG. 4, which corresponds to a large extent to that for the compact object 70 in three dimensions.

A linear object 70 of this kind may be determined precisely in its orientation if the axis 71, which is a straight line, is determined precisely by two points. This may be achieved in that intersection points of the linear object 70 with two planes, which are spaced apart from one another, are ascertained.

The magnetic resonance tomography unit 1 is to ascertain these two planes in act S05. The magnetic resonance tomography unit 1 may, for example, have stored data from a treatment plan or from a user input. The stored data specifies a rough, error-prone location and position of the object 70. In one embodiment, the magnetic resonance tomography unit determines the location roughly with an error-prone conventional sequence of the magnetic resonance tomography unit 1. Based on this location, the magnetic resonance tomography unit 1 may use linear algebra means to ascertain a first plane 72 and a second plane 73 that, with certainty, have in each case an intersection point with the object 70 (e.g., by taking into consideration safety distances of the planes to the extremal coordinates of the object 70). The planes may be parallel to one another and at right angles to the axis 71, but other arrangements may also be provided as long as the planes do not coincide and are not aligned parallel to the axis 71.

In act S10, the magnetic resonance tomography unit uses an excitation pulse to excite nuclear spins in a region surrounding the compact metallic object. The excitation takes place according to the present embodiments in accordance with the bSSFP sequence used. In contrast to the method from FIG. 2, only 2D samplings of the planes take place in this embodiment of the method. The excitation pulse for the planes 72, 73 may be a slice excitation pulse under corresponding gradient fields for selection of a slice in the respective plane.

In a further act S50, the magnetic resonance tomography unit 1 acquires magnetic resonance data by sampling along a trajectory 90 in the first plane 72, as shown in FIG. 5. The trajectories 90 in the first plane 72 and the second plane 73 are accordingly likewise arranged in a plane in the k-space.

As already explained with reference to FIG. 2, the trajectories 90 may be radial trajectories 90 and may be distributed evenly, for example, over a full circle about the zero point in the plane 72, 73 in order to achieve the advantageous effect of symmetry of the artifacts in the mapping. Alternatively, this advantageous effect may also be achieved in a plane 72, 73 in that the trajectory 90 is sampled in each case in both directions, even if it is not a radial trajectory 90 but instead runs for example parallel to the Cartesian coordinates.

The nuclear spins are, for example, dephased in act S51 using a gradient in the first plane 72 in order to hide the background of the body. Only the region immediately surrounding the object is not affected by the magnetic field changes produced by the susceptibility difference, as the duration and/or strength of the gradient is selected precisely so that the duration and/or strength of the gradient dephase the magnetic resonance signals in the unaffected, more remote tissue.

In act S52, the magnetic resonance tomography unit acquires MR signals with a sampling scheme in the first plane 72 along a radial trajectory 90 in the k-space.

Further, in act S53, the magnetic resonance tomography unit acquires MR signals with a sampling scheme along the radial trajectory 90 in the opposite direction in the k-space.

The acts S52 and S53 are repeated for each trajectory 90 in the first plane 72.

Then, in act S60, image reconstruction takes place with the ascertained MR signals in the magnetic resonance tomography unit 1 or on an external device in the cloud 80 (e.g., a 2D image reconstruction for the first plane 72). The generated images show the metallic object essentially without background through the surrounding tissue on account of the white marker gradient or the dephasing of the object 70, albeit with the already mentioned artifacts such as distortion and dislocation.

In act S70, a focal point of the mapping of the object 70 in the first plane 72 is determined. A weighting factor may be applied to the position vectors, corresponding, for example, to a brightness value of the corresponding pixel. A threshold value function that considers only image points with an amplitude greater than a predetermined threshold value may also be provided.

In the bSSFP sequence used, the even distribution of the radial trajectories 90 or the acquisition of the trajectories 90 in both directions may result in a symmetrically mirrored distortion or dislocation in the image space, so that during the subsequent averaging, when the focal point is determined, these cancel each other out and are eliminated without quantitative knowledge of the distortion and dislocation when the focal point is determined.

Acts S50 to S70 are repeated as acts S80, S81, S82, S83, S90, and S100 in the same manner for the second plane 73. In one embodiment, the acts S50 to S70 and S80 to S100 may be carried out in parallel in a multislice acquisition for the first plane 72 and the second plane 73.

Two positions of the linear object 70 are determined with the focal points in both planes. An alignment may thus be determined as a straight line between the points and output to the user (e.g., in a representation of the patient or via an interface as an optical, acoustic, or tactile navigation aid).

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for localizing a metallic object that is compact in three dimensions or a linear metallic object that is compact in two dimensions using a magnetic resonance tomography unit, the method comprising:

exciting nuclear spins in a region surrounding the compact linear metallic object using an excitation pulse; and acquiring magnetic resonance data with samplings along a plurality of trajectories, wherein the nuclear spins are dephased by a gradient, wherein the samplings take place using a bSSFP sequence, wherein a position of a geometric focal point of the compact linear metallic object is ascertained based on a position of a visual focal point of acquired artifacts that are generated by the compact linear metallic object in a mapping reconstructed from the magnetic resonance data.

2. The method of claim 1, wherein the compact linear metallic object is spherically symmetrical, and the sampling is a three-dimensional (3D) sampling of a volume with the compact linear metallic object.

3. The method of claim 1, wherein the compact linear metallic object is a metallic object that is compact in two dimensions, wherein at least two two-dimensional (2D) samplings take place in two planes spaced apart along an axis of a longitudinal extension of the compact linear metallic object, and wherein the two planes intersect the compact linear metallic object.

4. The method of claim 1, wherein the magnetic resonance data is acquired for the plurality of samplings along radial trajectories, and wherein the plurality of trajectories are evenly distributed in an angle over a full circle in a plane through a center of the k-space or over a sphere about the center of the k-space.

5. The method of claim 1, wherein the plurality of trajectories are sampled in both directions.

6. A magnetic resonance tomography unit for localizing a metallic object that is compact in three dimensions or a linear metallic object that is compact in two dimensions, wherein the magnetic resonance tomography unit is configured to:

excite nuclear spins in a region surrounding the compact linear metallic object using an excitation pulse;

acquire magnetic resonance data with samplings along a plurality of trajectories;

dephase the nuclear spins using a gradient;

carry out the samplings using a bSSFP sequence;

ascertain a position of a geometric focal point of the compact linear metallic object based on a position of a visual focal point of an acquired artifact that is generated by the compact linear metallic object in a mapping reconstructed from the magnetic resonance data.

7. The magnetic resonance tomography unit of claim 6, wherein the sampling is a three-dimensional (3D) sampling of a volume with the compact linear metallic object.

8. The magnetic resonance tomography unit of claim 6, wherein the magnetic resonance tomography unit is further configured to carry out at least two two-dimensional (2D) samplings in two planes spaced apart along an axis of a longitudinal extension of the compact linear metallic object, and wherein the planes intersect the compact linear metallic object.

9. The magnetic resonance tomography unit of claim 6, wherein the magnetic resonance tomography unit is configured to acquire the magnetic resonance data for a plurality of samplings along radial trajectories, and wherein the plurality of trajectories are evenly distributed in an angle over a full circle in a plane through a center of the k-space or over a sphere about the center of the k-space.

10. The magnetic resonance tomography unit of claim 6, wherein the magnetic resonance tomography unit is further configured to sample the plurality of trajectories in both directions.

11. In a non-transitory computer-readable storage medium that stores instructions executable by a magnetic resonance tomography unit for localizing a metallic object that is compact in three dimensions or a linear metallic object that is compact in two dimensions, the instructions comprising:

exciting nuclear spins in a region surrounding the compact linear metallic object using an excitation pulse; and acquiring magnetic resonance data with samplings along a plurality of trajectories, wherein the nuclear spins are dephased by a gradient, wherein the samplings take place using a bSSFP sequence, wherein a position of a geometric focal point of the compact linear metallic object is ascertained based on a position of a visual focal point of acquired artifacts that are generated by the compact linear metallic object in a mapping reconstructed from the magnetic resonance data.

12. The non-transitory computer-readable storage medium of claim 11, wherein the compact linear metallic object is spherically symmetrical, and the sampling is a three-dimensional (3D) sampling of a volume with the compact linear metallic object.

13. The non-transitory computer-readable storage medium of claim 11, wherein the compact linear metallic object is a metallic object that is compact in two dimensions, wherein at least two two-dimensional (2D) samplings take place in two planes spaced apart along an axis of a longitudinal extension of the compact linear metallic object, and wherein the two planes intersect the compact linear metallic object.

14. The non-transitory computer-readable storage medium of claim 11, wherein the magnetic resonance data is acquired for the plurality of samplings along radial trajectories, and wherein the plurality of trajectories are evenly distributed in an angle over a full circle in a plane through a center of the k-space or over a sphere about the center of the k-space.

15. The non-transitory computer-readable storage medium of claim 11, wherein the plurality of trajectories are sampled in both directions.

* * * * *